United States Patent [19]

Quallich

[11] Patent Number: 5,576,442
[45] Date of Patent: Nov. 19, 1996

[54] PROCESS AND CHIRAL INTERMEDIATES FOR THIAZOLE ANTIDIABETICS

[75] Inventor: George J. Quallich, North Stonington, Conn.

[73] Assignee: Pfizer Inc., New York, N.Y.

[21] Appl. No.: 162,036

[22] PCT Filed: Jul. 1, 1992

[86] PCT No.: PCT/US92/05434

§ 371 Date: Dec. 2, 1993

§ 102(e) Date: Dec. 2, 1993

[87] PCT Pub. No.: WO93/02061

PCT Pub. Date: Feb. 4, 1993

Related U.S. Application Data

[63] Continuation of Ser. No. 733,548, Jul. 22, 1991, abandoned.

[51] Int. Cl.⁶ ............................................. C07D 277/24
[52] U.S. Cl. ............................................. 548/203
[58] Field of Search ............................................. 548/203

[56] References Cited

U.S. PATENT DOCUMENTS 4,886,814  12/1989  Reiffen et al. ............................. 514/326
4,943,635  7/1990  Corey.
5,036,079  9/1991  Clark.
5,512,689  4/1996  Quallich ............................. 548/235

OTHER PUBLICATIONS

Corey et al., Journal of the American Chemical Society, 1987, 109, 5551–3.

Corey et al., Journal of the American Society, 1987, 109, 7925–6.

Jones et al., Journal of Organic Chemistry, 1991, 56, 763–9.

Quallich et al, Tet. Letters 34(5) 785 (1993).

Lancaster Catalogue 1991/2 p. 888.

*Primary Examiner*—Robert Gerstl
*Attorney, Agent, or Firm*—Peter C. Richardson; Gregg C. Benson; Robert T. Ronau

[57] ABSTRACT

Two novel optically pure intermediates, (R)-4-(2-bromo-1-hydroxyethyl)-2- trifluoro(-)methylthiazole and (S)-4-oxiranyl-2-trifluoromethylthiazole, which have utility in the synthesis of a potent class of antidiabetic agents. The invention also embraces an enantioselective reduction process for their preparation.

10 Claims, No Drawings

PROCESS AND CHIRAL INTERMEDIATES FOR THIAZOLE ANTIDIABETICS

CROSS REFERENCE TO RELATED APPLICATIONS

This is a continuation of co-pending International Application No. PCT/US92/0534, filed on Jul. 01, 1992, entitled "Process and Chiral Intermediates for Thiazole Antidiabetics," which is a continuation of U.S. Ser. No. 07/733,548, filed on Jul. 22, 1991, entitled "Process and Chiral Intermediates for Thiazole Antidiabetics" (now abandoned).

BACKGROUND OF THE INVENTION

The compound depicted in formula I and related compounds have been reported in U.S. 4,886,814 to have utility as antidiabetics.

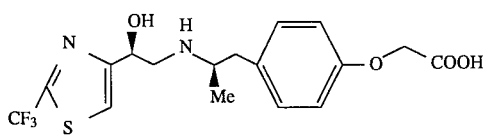

The present invention relates to novel key intermediates in the synthesis of compound I, said intermediates being (R)-4-(2-bromo-1-hydroxyethyl)-2-trifluoromethylthiazole (II) and (S)-4-oxiranyl-2-trifluoromethylthiazole (III), and to an enantioselective reduction process for the preparation of these compounds which results in their being obtained essentially free of their enantiomeric forms.

The racemic form of the bromohydrin (II), depicted below, has been reported. Within the same reference, the racemic form of the epoxide has also been reported. However, the S-bromohydrin (II) and the (S)-epoxide (III) are both previously unknown in their purified chiral forms.

It is advantageous to prepare the bromohydrin and epoxide in optically pure form since the final product of formula I has the S configuration at the hydroxyl-substituted chiral center. Therefore, a process whereby the desired stereochemistry is directly obtained is highly desirable.

The stereoselective reduction process of this invention involves the use of a borane reducing agent and a chiral oxazaborolidine catalyst. Corey, et al. (Journal of the American Chemical Society, 1987, 109, 5551–3 and 7925–6) have described generally the reduction of a limited number of ketones with boranes utilizing chiral oxazaborolidines to elicit enantioselectivity. However, recent studies by Jones, et al. (Journal of Organic Chemistry, 1991, 56, 763–9) have demonstrated that the method loses its effectiveness when molecules possessing borane coordination sites are present in the reaction mixture. Examples of compounds containing borane coordination sites include but are not limited to such compounds as boronic acids, boroxines, prolinols, amines, thiazoles and oxazoles. This loss of effectiveness is manifested in diminished enantioselectivity. The present invention is directed to a process in which the deleterious effect of said borane coordination sites has been overcome.

SUMMARY OF THE INVENTION

This invention is directed to (R)-4-(2-bromo-1-hydroxyethyl)-2-trifluoromethylthiazole (II) and (S)-4-oxiranyl-2-trifluoromethylthiazole (III), both compounds being substantially free of their corresponding R enantiomer.

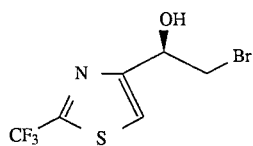

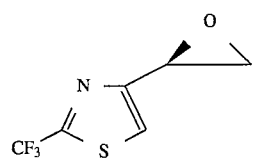

Also embraced by the invention is a process for the enantioselective preparation of the above-mentioned compounds from the achiral ketone precursor IV.

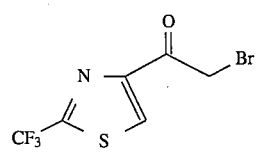

Thus, said ketone IV is enantioselectively reduced using a borane reducing agent such as borane methyl sulfide complex, catecholborane or borane-tetrahydrofuran in the presence Of a chiral oxazaborole catalyst in a cyclic ether solvent such as dioxane or tetrahydrofuran to afford, in essentially optically pure form, (R)-4-(2-bromo-1-hydroxyethyl)-2-trifluoromethylthiazole (II). A preferred reducing agent is borane-methyl sulfide complex; a preferred catalyst is (R)-tetrahydro-1-methyl-3,3-diphenyl-1H,3H-pyrrolo[1,2-c][1,3,2]oxazaborole and a preferred solvent is tetrahydro solvent is tetrahydrofuran. The process of this invention results in achievement of a high percent enantiomeric excess.

The bromohydrin (II) is further elaborated to the optically pure (S)-4-oxiranyl-2trifluoromethylthiazole (III) by treatment with sodium hydroxide. This dehydrobromination affords the cyclized product without racemization of the chiral center.

DETAILED DESCRIPTION OF THE INVENTION

The present invention provides two novel, optically pure, key intermediates of structures II and III, depicted above. The depicted compounds, (R)-4-(2-bromo-1-hydroxyethyl)-2-trifluoromethylthiazole (II) and (S)-4-oxiranyl-2-trifluoromethylthiazole(III) are provided in optically pure form, substantially free of their corresponding enantiomers.

Also embraced by the invention is the enantioselective reduction process whereby compound II is prepared.

SCHEME I

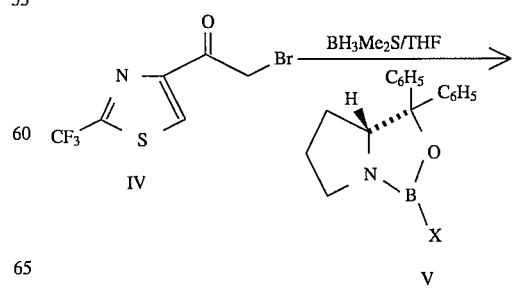

-continued
SCHEME I

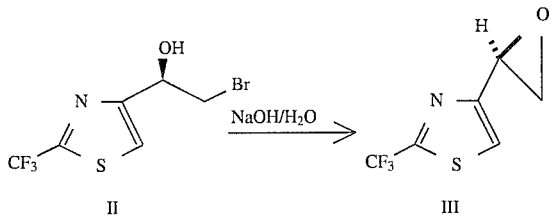

The process, see Scheme I, comprises treating the ketone, 4-bromoacetyl-2trifluoromethylthiazole, with about 1.1 to 2.0 molar equivalents of a borane reducing agent in the presence of a chiral oxazaborolidine catalyst in a cyclic ether solvent at −20° C. to +40° C. Examples of suitable borane reducing agents include but are not limited to borane methyl sulfide complex, catecholborane, and borane tetrahydrofuran. Most preferred is the system in which borane methyl sulfide complex is utilized. The term "chiral oxazaborolidine catalyst" is meant to define compounds of general structure V, wherein X is $(C_1-C_4)$alkyl, phenyl or $(C_7-C_9)$phenylalkyl. Preferred is the case where X is methyl, n-butyl or phenyl. Most preferred is the instance in which X is methyl. The R stereochemistry depicted in the catalyst of formula V is critical to the production of the desired R stereochemistry in the product bromohydrin (II). The term "cyclic ether solvent" is defined as any C-4 to C-6 cycloalkane containing either one or two oxygens Within the ring, such as tetrahydrofuran or dioxane. More preferred is tetrahydrofuran. The ideal temperature for the reaction is ambient temperature, ambient temperature being defined as the temperature of the room within which the reaction is being carded out, when that temperature falls within the range of +18° C. to +25° C.

Progress of the reaction is monitored by methods well-known to those skilled in the art. Such monitoring indicates that the reduction is generally complete after a period of time ranging from 15 minutes to 3 hours, including addition of reagents. At this time the reaction mixture is cooled to 0° C. and quenched by the careful (dropwise) addition of methanol. Isolation and purification is easily accomplished by means of well-established procedures known to those skilled in the art, affording the (R)-bromohydrin (II) substantially free of its S enantiomer.

The process further comprises treatment of the optically pure (R)-4-(2-bromo-1-hydroxyethyl)-2-trifluoromethyl-thiazole with sodium hydroxide to effect dehydrobromination and concomitant cyclization to the optically pure (S)-4-oxiranyl-2-trifluoromethylthiazole (III), without racemization of the chiral center.

The ketone starting material (IV) for this process is readily prepared from commercially available materials by following the known procedure (U.S. 4,886,814). Reaction of trifluoromethyl acetamide with Lawesson's Reagent in dimethoxyethane yields the thioacetamide derivative, which is transformed to 4-bromoacetyl-2trifluoromethylthiazole (IV) by reaction with 1,4-dibromo-2,3-butanedione in acetonitrile.

The (S)-epoxide (III ), which is the product of the process of the present invention, is elaborated to the aforementioned antidiabetic agent of formula I by reaction with the compound of formula VI in methanol to yield the epoxide-ring-opened product (VII) as shown in Scheme II (supra).

The chemistry used to elaborate the ring-opened product (VII) to the final product is also reported in the aforementioned patent. Thus, reaction of VII with HCl(g) in ethanol deprotects the phenol to give VIII, which is reacted with methylbromoacetate and potassium carbonate in acetone to give the O-alkylated material (IX). This material is hydrogenated with palladium on carbon in methanol and the resulting amine is saponified with 1N sodium hydroxide in methanol to afford the desired product (I).

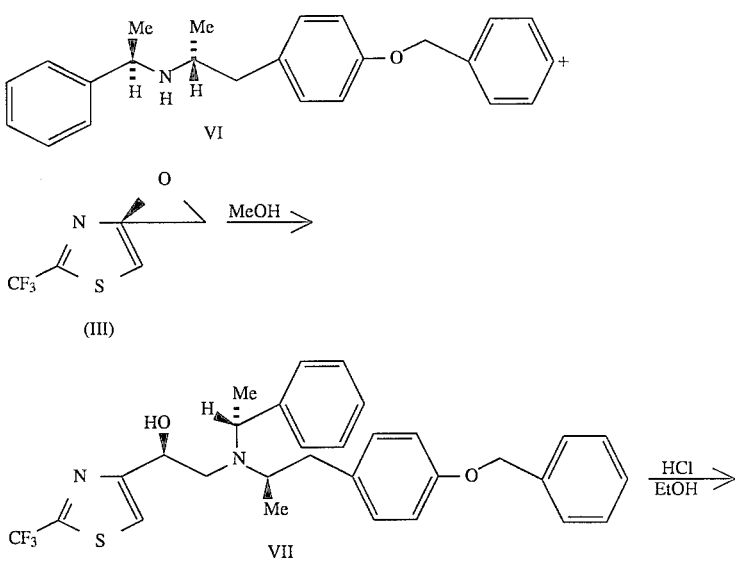

SCHEME II

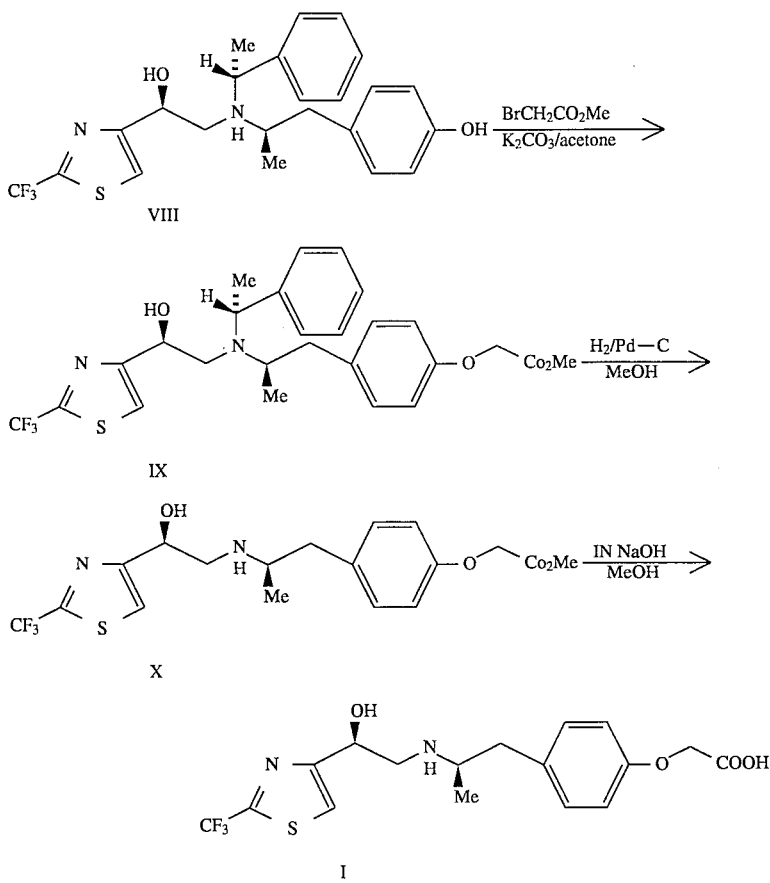

Elaboration to the antidiabetic compound of formula I is also accomplished by reaction of epoxide III with methyl O-[4-(2-aminopropyl)phenyl]glycolate to afford the penultimate compound of Scheme II directly. This compound is simply saponified with 1N NaOH to give compound I.

Methods of using compound I as an antidiabetic agent in humans are described in U.S. Pat. No. 4,886,814.

This invention is further illustrated by the following examples. However, it should be understood that the invention is not limited to the specific details of these examples.

EXAMPLE 1

(R)-4-(2-Bromo- 1-hydroxyethyl-2 -trifluoromethylthiazole

Borane methyl sulfide complex (2M in THF, 50 mL, 100 mmol) and 4-bromoacetyl-2-trifluoromethylthiazole (20.15 g, 73.5 mmol) were added separately and simultaneously over one our to (R)-tetrahydro-1,3,3-triphenyl-1H,3H-pyrrolo[1,2-c][1,3,2]oxazaborole (1.2 g, 3.53 mmol) in tetrahydrofuran (50 mL) at ambient temperature. After the reduction was complete the reaction mixture was cooled to 0° C. and quenched with methanol (dropwise addition of 115 mL) while maintaining the temperature at less than or equal to 13° C. The quenched reaction mixture was stirred at 5° to 10° C. for ten minutes and then at ambient temperature for 45 minutes. The solvents were removed in vacuo and the residue was dissolved in methylene chloride (180 mL), washed with pH 4 aqueous phosphate buffer (180 mL), water (180 mL) and dried (MgSO$_4$). The solvent was removed in vacuo to afford 4-(2-bromo-1-hydroxyethyl)-2-trifluoromethylthiazole as an amber oil (20.14 g, 99%, 90% ee). $^1$NMR (300 MHz, CDCl$_3$): $\delta$7.61 (s, 1H), 5.13 (dd, J=4 Hz, J=7 Hz, 1H), 3.91 (dd, J=4 Hz, J=10 Hz, 1H), 3.70 (dd, J=7 Hz, J=10 Hz, 1H), 2.88 (bs, 1H).

EXAMPLE 2

(R)-4-(2-Bromo) 1-hydroxyethyl-2-trifluorothiazole

Borane-methyl sulfide complex (2M in THF, 1.4 eq., 2.74 mL, 5.48 mmol) was added dropwise to a solution of 4-bromoacetyl-2-trifluoromethylthiazole (2.05 g, 7.48 mmol) and (R)-tetrahydro- 1 -methyl-3,3-diphenyl- 1H, 3H-pyrrolo [1,2 -c ][1,3,2]oxazaborole (56 mg, 0.20 mmol) in tetrahydrofuran (16 mL) at ambient temperature. After addition was complete (one hour), the reaction mixture was stirred for an additional 75 minutes, cooled to 0° C., and quenched by dropwise addition of methanol (10 mL). The quenched reaction mixture was stirred for 15 minutes at 0° C. and for 45 minutes at ambient temperature. The solvents were removed in vacuo and the residue was partitioned between methylene chloride (20 mL) and pH4 aqueous phosphate buffer (20 mL). The layers were separated and the organic phase was washed with water (20 mL) and dried (MgSO$_4$) to afford the crude product as a yellow oil (1.10 g, 102%, 94% ee), $\alpha$D=−19.25° (C=1 acetone). $^1$HNMR (300 MHz, CDCl$_3$): $\delta$7.61 (s, 1H), 5.13 (dd, J=4 Hz, J-7 Hz, 1H), 3.91 (dd, J=4 Hz, J=10 Hz, 1H), 3.70 (dd, J=7 Hz, J=10 Hz, 1H), 2.88 (be, 1H).

EXAMPLE 3

(R)-4-(2-Bromo)-1-hydroxyethyl-2-trifluoroethylthiazole

Borane-methyl sulfide complex (2M in THF, 1.4 eq., 5.2 mL, 10.6 mmol) was added dropwise to a solution of 4-bromoacetyl-2-trifluorothiazole (2.05 g, 7.48 mmole) and (R)-tetrahydro-1-n-butyl-3,3-diphenyl-1H,3H-pyrrolo[1,2-c][1,3,2]oxazaborole (129 mg, 0.40 mmol) in tetrahydrofuran (30 mL) at ambient temperature. After addition was complete (one hour), the reaction mixture was stirred an additional one hour, cooled to 0° C., and quenched by dropwise addition of Methanol (20 mL). The quenched reaction mixture was stirred for 16 hours and allowed to warm to ambient temperature. The solvents were removed in vacuo and the residue was partitioned between methylene chloride (30 mL) and pH 4 aqueous phosphate buffer (30 mL). The layers were separated and the organic phase was washed with water (30 mL) and dried ($MgSO_4$) to afford the crude product as a pale yellow oil (2.083 g, 100%, 88% ee). $[\alpha]_D = 17.7°$ (C=1 acetone). $^1$HNMR (300 MHz, $CDCl_3$): δ7.61 (s, 1H), 5.13 (dd, J=4 Hz, J=7 Hz, 1H), 3.91 (dd, J=4 Hz, J=10 Hz, 1H), 3.70 (dd, J=7 Hz, J=10 Hz, 1H), 2.88 (bs,

EXAMPLE 4

(S)-4-Oxiranyl-2-trifluoromethylthiazole

The title compound of example one (20.07 g, 72.7 mmol), neat, with vigorous stirring, was treated with sodium hydroxide (4N, 18.7 mL) at ambient temperature. The reaction mixture was stirred for ten minutes after which time methylene chloride (200 mL) and water (200 mL) were added. The layers were separated and the organic layer was washed three times with 200 mL of water and dried ($MgSO_4$). The solvent was removed in vacuo and the residue was purified on silica gel (elution with methylene chloride) to afford 4-oxiranyl-2-trifluoromethylthiazole as a light yellow oil (10.15 g, 71%), $[\alpha]=-10.96°$ (C=1.31, $CH_2Cl_2$).

I claim:

1. A process for the stereoselective preparation of the compound of the formula

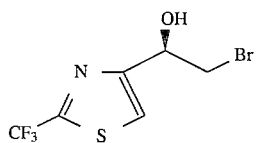

which comprises treating a ketone of formula III,

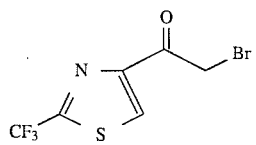

with about 1.1–2.0 molar equivalents of a borane reducing agent in the presence of a chiral oxazaborolidine catalyst in a cyclic ether solvent at a temperature of about −20° C. to about 40° C.

2. The process of claim 1 wherein the cyclic ether solvent is tetrahydrofuran.

3. The process of claim 2 wherein the temperature of the reaction mixture is ambient temperature.

4. The process of claim 3 wherein said oxazaborolidine catalyst is a compound of formula V,

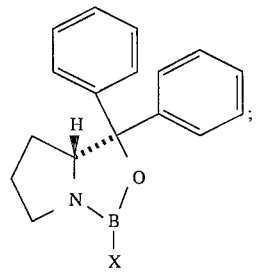

wherein X is ($C_1$–$C_4$)alkyl, phenyl or ($C_7$–$C_9$)phenylalkyl.

5. The process of claim 4 wherein X is methyl, phenyl or n-butyl.

6. The process of claim 5 wherein said borane reducing agent is borane-methyl sulfide complex.

7. The process of claim 6 wherein X is methyl.

8. The process of claim 6 wherein X is n-butyl.

9. The process of claim 6 wherein X is phenyl.

10. The process of claim 1, which further comprises the additional, subsequent step of treating said compound of claim 1 with sodium hydroxide to obtain the epoxide of claim 2.

* * * * *

UNITED STATES PATENT AND TRADEMARK OFFICE
CERTIFICATE OF CORRECTION

PATENT NO. : 5,576,442

DATED : NOVEMBER 19, 1996

INVENTOR(S) : GEORGE J. QUALLICH

It is certified that error appears in the above-identified patent and that said Letters Patent is hereby corrected as shown below:

In claim 1, column 8, line 1, immediately after the word "formula" delete "III" and replace it with --IV--.

In claim 1, column 8, line 3, adjacent to the structure 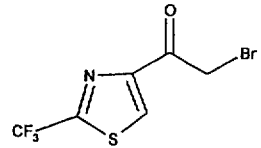 delete "III" and replace it with --IV--.

In claim 10, column 8, line 44, immediately after the phrase "said compound of", delete the phrase "claim 1" and replace it with --formula II,

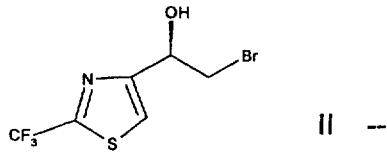   II --

UNITED STATES PATENT AND TRADEMARK OFFICE
CERTIFICATE OF CORRECTION

PATENT NO. : 5,576,442
DATED : November 19, 1996
INVENTOR(S) : George J. Quallich It is certified that error appears in the above-indentified patent and that said Letters Patent is hereby corrected as shown below:

In claim 10, column 8, line 45, immediately after the phrase "the epoxide of", delete the phrase "claim 2" and replace it with --formula III,

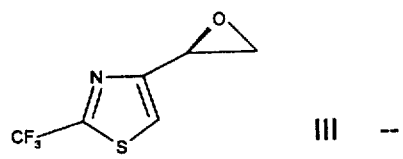   III --

Signed and Sealed this

Sixth Day of May, 1997

Attest:

BRUCE LEHMAN

Attesting Officer

Commissioner of Patents and Trademarks